US006349724B1

United States Patent
Burton et al.

(10) Patent No.: US 6,349,724 B1
(45) Date of Patent: Feb. 26, 2002

(54) DUAL-PRESSURE BLOWER FOR POSITIVE AIR PRESSURE DEVICE

(75) Inventors: David Burton, Camberwell; Allan Wallace, South Australia, both of (AU)

(73) Assignee: Compumedics Sleep PTY. Ltd., Abbotsford (AU)

( * ) Notice: Subject to any disclaimer, the term of this patent is extended or adjusted under 35 U.S.C. 154(b) by 0 days.

(21) Appl. No.: 09/610,446

(22) Filed: Jul. 5, 2000

(51) Int. Cl.$^7$ ............................................ A61M 16/00
(52) U.S. Cl. ............................ 128/204.18; 128/204.22; 128/204.24
(58) Field of Search .......... 128/204.18, 200.11–207.12; 137/565.29–565.33

(56) References Cited

U.S. PATENT DOCUMENTS

| | | | |
|---|---|---|---|
| 3,257,954 A | 6/1966 | Millburn et al. ............... | 103/87 |
| 3,337,122 A | 8/1967 | Gross .......................... | 230/117 |
| 3,612,717 A * | 10/1971 | Burns .......................... | 415/219 |
| 3,805,731 A | 4/1974 | Furst et al. .................... | 115/16 |
| 4,061,187 A * | 12/1977 | Rajasekaran et al. ......... | 165/107 |
| 4,404,177 A | 9/1983 | Derbyshire et al. .......... | 423/448 |
| 4,463,764 A | 8/1984 | Anderson et al. ............. | 128/719 |
| 4,653,976 A * | 3/1987 | Blair et al. .................... | 415/1 |
| 4,796,639 A | 1/1989 | Snow et al. ................. | 128/719 |
| 4,799,855 A | 1/1989 | Milocco et al. ............. | 415/143 |
| 4,887,940 A * | 12/1989 | Todoroki et al. ......... | 415/199.1 |
| 4,930,979 A | 6/1990 | Fisher et al. ................ | 415/58.4 |
| 5,235,803 A * | 8/1993 | Rodgers ..................... | 60/39.07 |
| 5,485,850 A | 1/1996 | Dietz .......................... | 128/716 |
| RE35,295 E | 7/1996 | Estes et al. ............. | 128/204.23 |

FOREIGN PATENT DOCUMENTS

| | | | |
|---|---|---|---|
| WO | WO 97/16216 | 5/1997 | .......... A61M/16/00 |
| WO | WO 98/50095 | 11/1998 | .......... A61M/16/00 |

* cited by examiner

*Primary Examiner*—John G. Weiss
*Assistant Examiner*—Virendra K Srivastava
(74) *Attorney, Agent, or Firm*—Nikolai & Mersereau, P.A.

(57) ABSTRACT

A gas compression and delivery device for treatment of sleep disorders. The device has a motor, at least one impeller, and two air pressure chambers, each receiving air at a different pressure, one pressure applied to a patient during inspiration and one for expiration. A mask having a dual pressure gas delivery hose and a selector for letting in either the high or low pressure gas depending on the breathing cycle of the patient. The gas pressures are adjustable by means of valves on the separate chambers in the device. At least one sensor on the patient sending data to a controller in the device as to the patient's physiological data which is used to determine the patients breathing treatment needs. The controller may be a microprocessor with memory capability to store patient data for diagnosis and treatment of the patient. Telecommunications by telemetry, or telephony to a remote site allows home use of the device rather than institutional use with health care providers on site. A data card may be used to input and or store data in the device. The controller is capable of instructing the device to treat the patient with a number of different protocols and record the patient's physiological data for diagnosis and treatment purposes.

34 Claims, 4 Drawing Sheets

DUAL-PRESSURE BLOWER FOR POSITIVE AIR PRESSURE DEVICE

BACKGROUND OF THE INVENTION

1. Field of the Invention

This invention relates to a dual pressure pump having at least one impeller producing two separate pressures in two separate chambers. The dual pressures are used for positive air pressure treatments in patients with sleep disorders. One pressure is used during inspiration and one pressure is used during expiration.

2. Description of the Related Art

There are many Bi-Positive Air Pressure (Bi PAP) devices used for treatment of sleep apnea, and other sleep disorders. These devices mostly use a variable speed motor with one blower to increase and decrease the air pressure applied to the patient or use valves to regulate the air pressure applied to the patient.

The devices with variable speed motors take a while to change the pressure applied to the patient, as the motor speed does not change instantaneously between the inspiration and expiration pressure settings. Similarly valves regulating the pressure in a chamber have a lag time while pressure is building up or reducing before it reaches the proper pressure to be applied to the patient.

U.S. Pat. No. 5,485,850 to Dietz issued Jan. 23, 1996 shows a Bi PAP device with two separate air supply sources at two different pressures.

A device is needed having one unit for supplying dual pressures to the patient such that there is always a ready supply of air at two different pressures to treat a patient.

SUMMARY OF THE INVENTION

The invention comprises a motor with at least one impeller. The impeller or impellers produce a different air pressure in different chambers. A hose transports the air from the chambers to the mask worn by the patient to deliver air at one pressure for use during inspiration and at another pressure during expiration. A valve selects which pressure to allow into the mask depending on if the patient is inhaling or exhaling. There is a means for detecting if the patient is inhaling or exhaling which regulates the valve. There are also means for measuring the airflow into and out of the patient.

A humidifier can adjust the humidity of the air being delivered to the patient.

Altitude adjustments are made to increase or decrease the impeller speed to deliver the correct air pressure to the patient.

The two chambers can have two pressures at adjustable ratios to adjust the inspiration and expiration pressures.

The patient can be monitored by a number of sensors for determining when the patient is inhaling or exhaling. The monitoring sensors can also measure a number of other parameters such as breathing rates, blood oxygen levels, stages of sleep, mask leaks, mask on or mask off, body position and movement of the patient, EEG, EKG, sounds such as snoring, and other information useful for sleep disorder diagnosis and treatment. The information obtained can be used in conjunction with adjusting pressures and times of delivery of air to the patient in real time, adjusting for mask leaks, storing information about the patient for diagnosis and long-term studies, or for alerting health care workers about the patent's condition requiring immediate action.

The sensors can trigger a mask off alarm or detect when the mask is put on to start the power for the motor to supply air to the patient.

A controller or microprocessor programmed to evaluate the data from the sensors on the patient, can make changes to the air pressure applied to the patient, and the timing thereof. The microprocessor can also store information for later reporting, transmit the data to recording equipment, or alert health care workers of the patient's condition.

Displays can provide data for the number of hours the motor has been on or other data of interest to the operator.

Data cards for input or output of data may be used. Data from the data card may be sent to a remote site by telemetry, telephony or by mailing the data card.

The device may be equipped with anti-rebreathing sensors and apparatus to ensure fresh air inspiration.

The device is portable, light weight and easy to use by a patient without the assistance of a health care provider such that the device can be used at home and monitored at a remote location.

OBJECTS OF THE INVENTION

It is an object of the invention to provide a dual air pressure pump with one motor having at least one impeller.

It is an object of the invention to provide accurate pressure control for inspiration and expiration gas delivery pressures.

It is an object of the invention to provide fast transitions between inspiration and expiration pressures delivered to the patient.

It is an object of the invention to provide a portable BiPAP device. It is an object of the invention to provide a multiple purpose device for BiPAP, CPAP, VPAP, SPAP, PPAP and AutoPAP applications.

It is an object of the invention to add humidity to the pressurized air.

It is an object of the invention to monitor the patient.

It is an object of the invention to measure airflow to and from the patient.

It is an object of the invention to record patient data for diagnosis and treatment.

It is an object of the invention to provide data storing cards for use in the device.

It is an object of the invention to communicate patient condition to remote monitoring equipment and personnel.

It is an object of the invention to treat a variety of sleep disorders with a variety of treatments with one device.

It is an object of the invention to provide options for several different treatment protocols on one device.

It is an object of the invention to provide adjustable settings for individual patient needs and comfort while using the device.

It is an object of the invention to provide long term monitoring data of one or more patients for medical studies.

It is an object of the invention to display data about the patient or devise for ease of reference.

It is an object of the invention to provide variable ratios of air pressure for inspiration and expiration.

Other objects, advantages and novel features of the present invention will become apparent from the following detailed description of the invention when considered in conjunction with the accompanying drawings.

DESCRIPTION OF THE PREFERRED EMBODIMENTS

Figure 1:
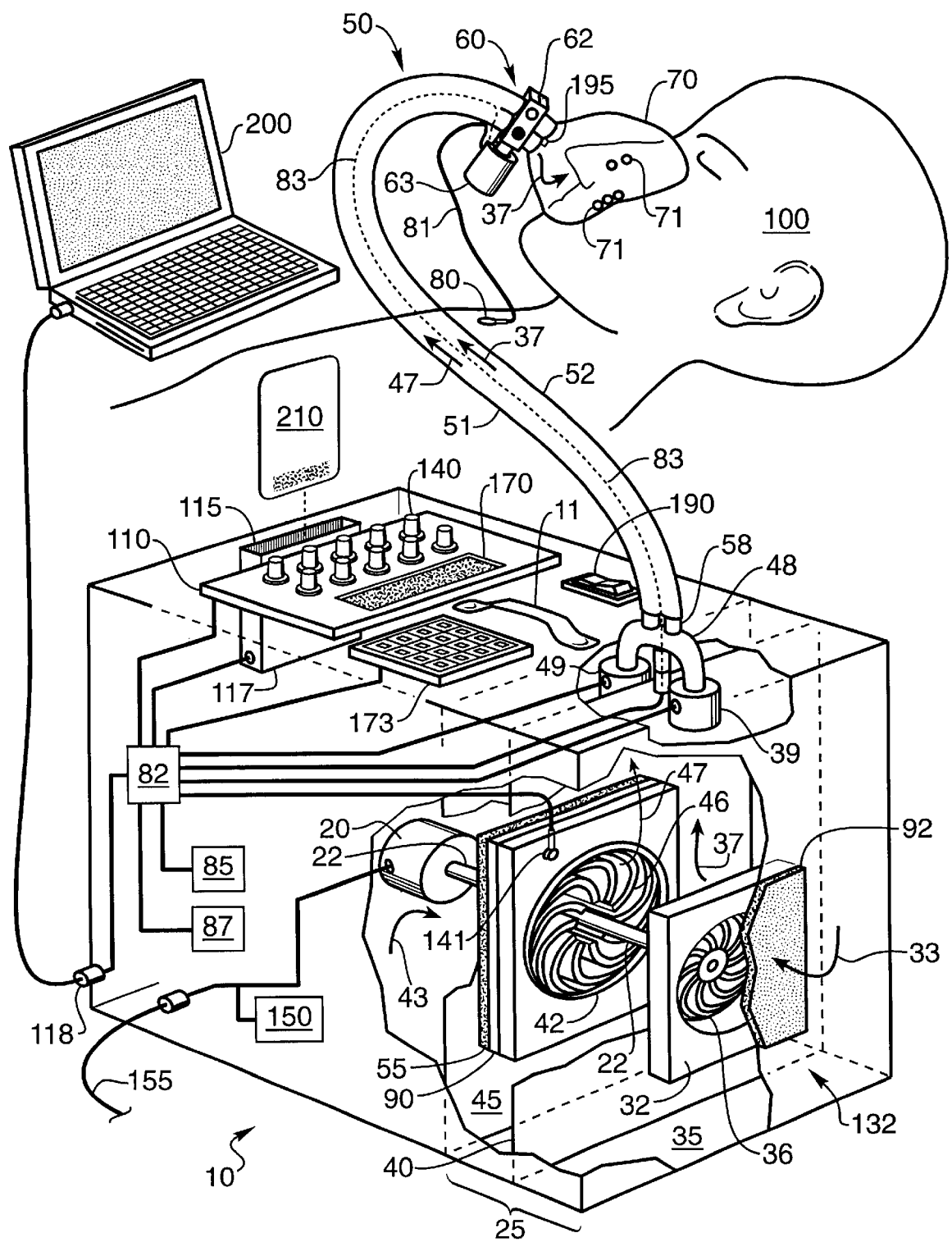
FIG. 1 is a schematic showing the device with two separate air intakes and two separated impellers.

In treating patients having sleep disorders it is frequently required to administer a Bi-Positive Air Pressure (Bi PAP). In this treatment a first air pressure on the order of 20 cm $H_2O$ is applied to the patient during inspiration and a second pressure on the order of 3 cm $H_2O$ is applied to the patient during expiration. Preferably these pressures are adjustable for the needs of each individual patient. Referring to FIG. 1 a schematic of the system is shown wherein a gas delivery device 10 supplies gas at two different positive air pressures to a patient 100. The gas delivery device 10, preferably is small enough and light weight enough to be portable. The gas delivery device 10 has a carrying handle 11 to aid in transporting the device.

A portable gas delivery device may have a battery 150 for an internal power supply, a power cord 155 for an outside source of power, or both. The battery 150 may be rechargeable from the outside power source.

A motor 20 receiving power from the battery 150 or an outside power source through the power cord 155 turns shaft 22. The motor 20 is preferably a brushless DC motor. Motor with brushes and a commutators produce ozone or NOx and other related particles which would be detrimental if added to the air of the breathing apparatus. The shaft 22 enters the pump housing 25 having a high pressure chamber 45 and a low pressure chamber 35 which are adjacent, having a barrier 40 therebetween. The shaft 22 turns high pressure impeller blades 46 in the high pressure chamber 45 and turns low pressure impeller blades 36 in the low pressure chamber 35. The air intake aperture 142 for the high pressure chamber 45 has air filter 90 for filtering intake air stream 43 entering the high pressure chamber 45. Similarly air intake aperture 132 for the low pressure chamber 35 has air filter 92 for filtering intake air stream 33.

Alternatively the air intake can be a common air intake if the impellers 36 and 46 in FIG. 1 are turned around such that the air intake is between them and the air output would be to chambers which are separate.

The ratio of the high pressure in chamber 45 to the low pressure in chamber 35 is fixed by the relative size or position of the impeller blades. The ratio can be changed by varying a number of parameters including the relative size of the impellers, the gaps between the impellers and the housings, the size of the openings in the housings for admitting air from the impellers, or by other variables. The ratios may be adjustable or fixed. Generally for one patient the ratio of the inspiration pressure to the expiration pressure can remain fixed. It may be necessary to adjust the ratios for different patients or adjust the ratios for the same patient over time.

A humidifier 55 may be used to adjust the humidity of the air being supplied to the patient. The humidifier 55, as shown in the dual pressure gas delivery device 10, is in front of the high pressure air intake aperture 142 to supply moisturized air for inspiration. The humidifier 55 may be placed in other locations for supplying high pressure and/or low pressure moisturized air to the patient. A humidity control 140 to select the desired humidity is located on the control panel 110 and works in conjunction with humidity sensors 141 in housing 25 and the controller or microprocessor 82 to keep the humidity at a desired setting.

Figure 2:
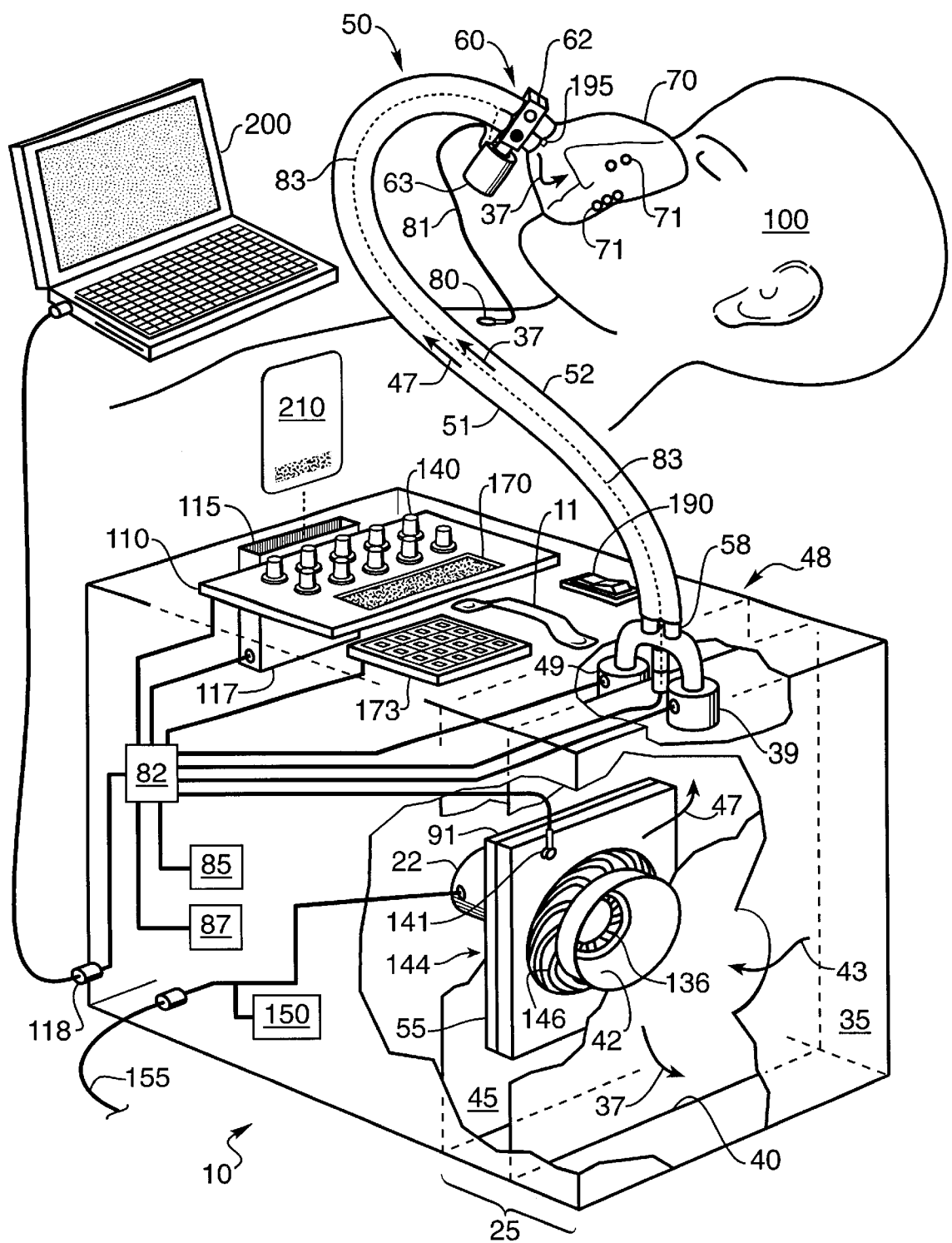
FIG. 2 is a schematic of a second embodiment showing the device with one air intake and two coaxial impellers.
Figure 3:
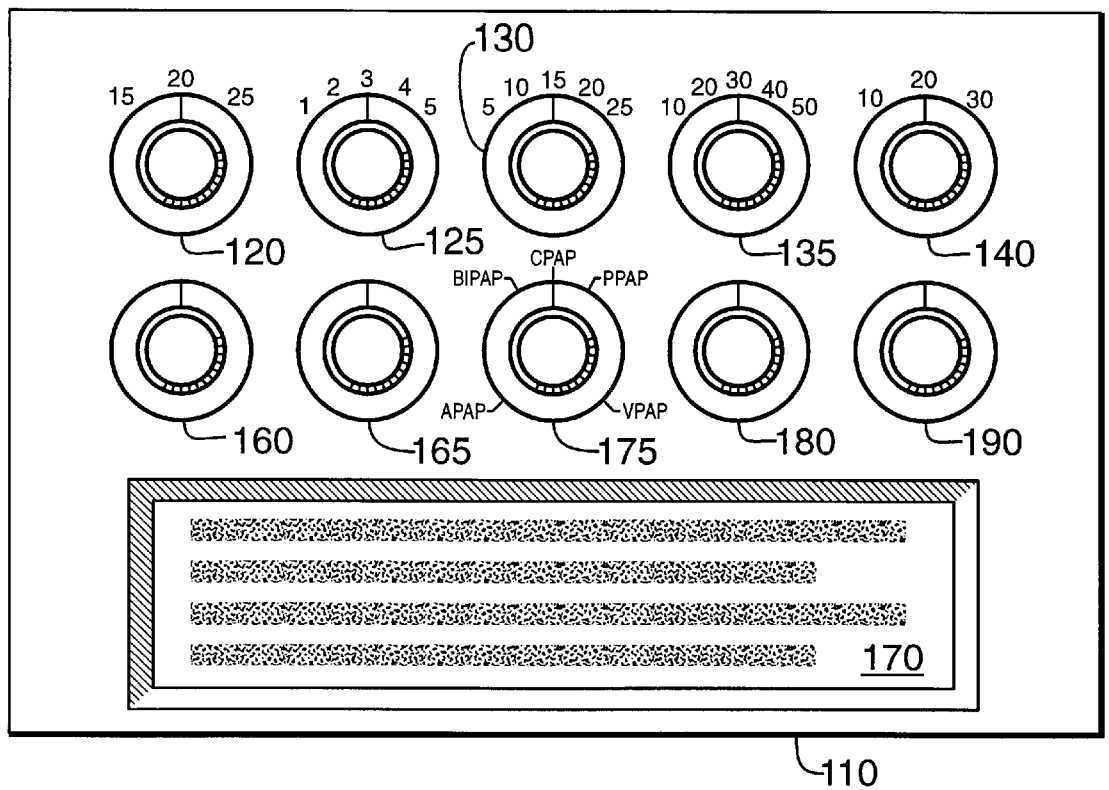
FIG. 3 is a top view of the control panel.
Figure 4:
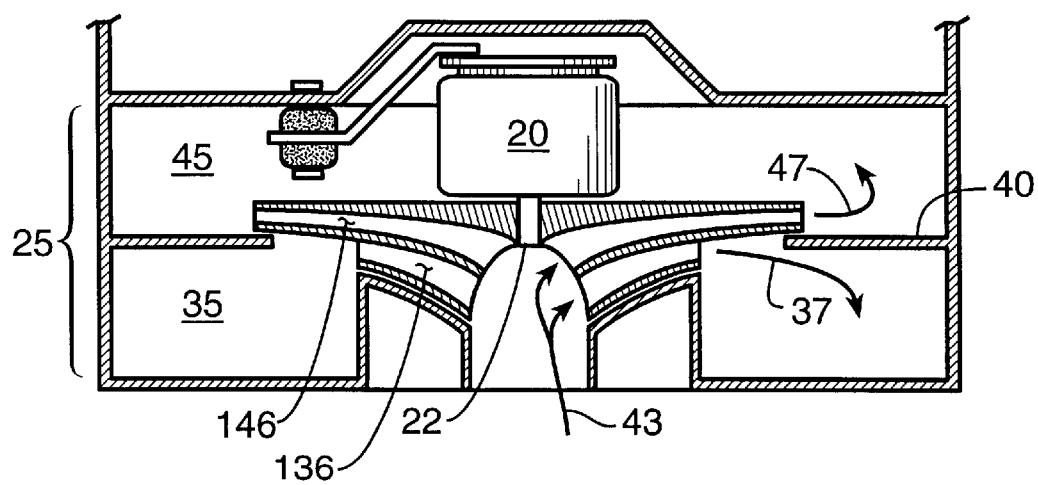
FIG. 4 is a side view of a coaxial dual impeller blower in a housing as used in the schematic of FIG. 2.

In a second embodiment shown in FIGS. 2 and 4 the motor 20 has a shaft 22 with impellers 136 of a first radius and impellers 146 of a second radius coaxially mounted on the shaft 22. There is one air intake 144 to the impellers 136, 146 for producing two streams of air, one at a high pressure, air stream 47 in chamber 45 and one at a low pressure, air stream 37 in chamber 35. Since this embodiment has only one air intake 144 only one air filter 91 and one humidifier 55 are required. FIG. 4 shows a more detailed view of the motor 20, high pressure impeller 146 and low pressure impeller 136 on shaft 22 in relation to housing 25. The intake air 43 enters housing 25. The low pressure impeller 136 discharges low pressure air 37 into low pressure chamber 35 and the high pressure impeller 146 discharges high pressure air 47 into the high pressure chamber 45.

Figure 5:
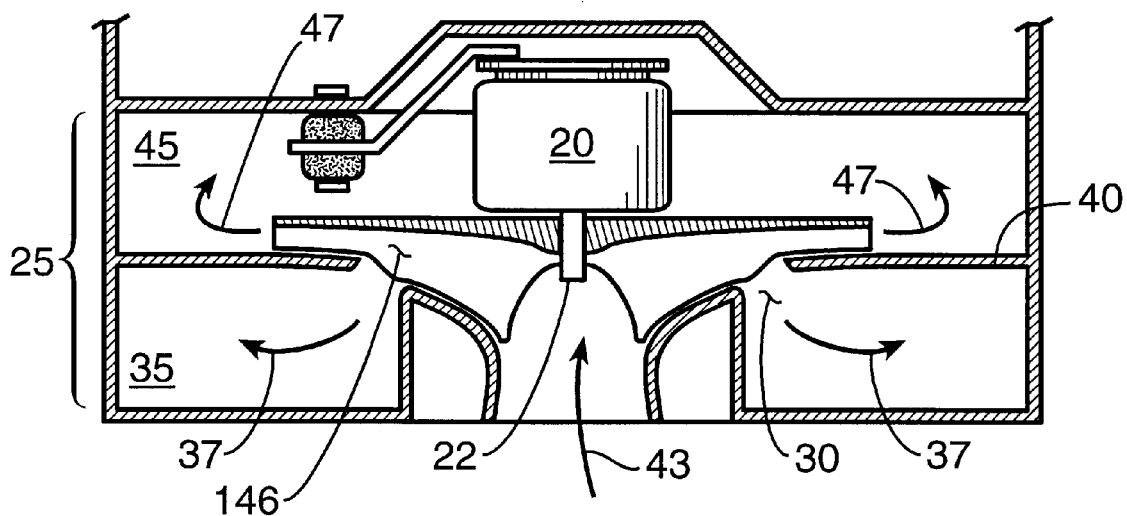
FIG. 5 is a cross sectional side view of one impeller in a housing with a bleed off slot.

In a third embodiment, as shown in FIG. 5, the motor 20 has shaft 22 attached to impeller 146. The housing has an annular slot 30 in the housing adjacent to impeller 146 to let air of a lower pressure into chamber 35. Intake air 43 is acted on by impeller 146 creating a high pressure air 47 in chamber 45 and low pressure air 37 in chamber 35. The annular slot 30 may be continuous or divided into sections.

The motor 20 in the three embodiments turns one or more impellers on shaft 22 for steadily supplying a high pressure air in the high pressure chamber 45 and a low pressure air chamber 35. On one embodiment the motor speed is fixed to supply a constant pressure in the high and low pressure chambers 45 and 35. In another embodiment a variable speed motor can be used to such that as the motor 20 speeds up or slows down a higher or lower volume of air is pumped and both the high pressure and low pressure are simultaneously adjusted upward or downward. A change in the motor speed can be used to make a pressure adjustment to the high pressure chamber 45 or low pressure chamber 35 when the ratio of the pressures is fixed but a variation or adjustment of the pressures in the chambers is called for. In this manner the high pressure and/or low pressure can be varied with changes in motor speed. Devices having one impeller and one pressure chamber would have to make large changes in motor speed and have a lag time to change speed and thereafter the pressure in the pressure chamber. A dual pressure impeller or two impellers with two pressure chambers do not require any motor speed change to change the pressure from high to low. However, adjustments to the pressure can still be effected by changing the motor speed.

Figure 6:
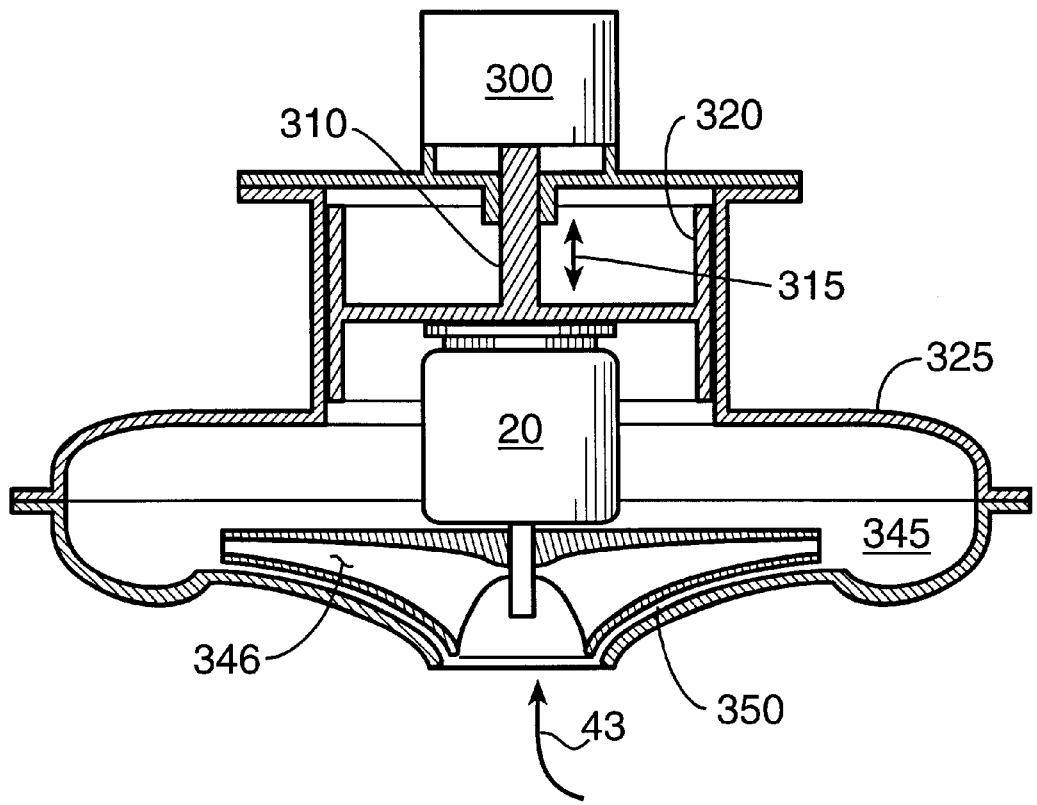
FIG. 6 is a cross sectional side view of a movable position impeller in a housing.

In a fourth embodiment shown in FIG. 6 an actuator 300 moves actuation rod 310 up or down by a small distance as shown by arrows 315. Actuator rod 310 is attached to slider 320 which moves up or down in housing 325. Slider 320 carries motor 20 and impeller 346 up and down adjusting the clearance distance 350 between the impeller and housing 325. With a larger clearance distance 350 the leakage rate of compressed air goes up reducing the air pressure in chamber 345. With a smaller clearance distance 350 the air pressure in chamber 345 goes up. The air intake 43 supplies air for the impeller 346 to pump up to the desired pressure in chamber 345. The actuator 300 can quickly and accurately adjust the clearance 350 between the impeller 346 and housing 325 thus quickly adjusting the pressure chamber 345 without changing the motor 20 speed.

The actuator 300 may be hydraulically, mechanically, electrically, electromechanically, or piezoelectrically driven. Any means for quickly and accurately moving the actuator rod 310 will allow the invention to be practiced.

The embodiment in FIG. 6 shows motor 20 on slider 320 however other embodiments where the motor is fixed and the actuator 300 only moves the impeller 346 are within the scope of the invention.

In all of the embodiments shown the motor 20 has shaft 22 connected to impeller an impeller, however in other embodiments the impellers can be on the outside of a rotating motor housing eliminating the need for a shaft 22.

Altitude compensation is required for the impeller speed to increase or decrease to bring the pressure up to the desired level. A pressure altitude sensor 85 senses the altitude and reports it to the controller 82, the controller then adjusts the motor speed accordingly. Altitude compensation can be controlled by a pressure transducer.

In the embodiments shown in FIGS. 1 and 2 if the pressure in the high pressure chamber 45 is kept at a pressure higher than needed for the patient 100 and the pressure in the low pressure chamber 35 is kept at a pressure higher than needed for the patient then a high pressure adjustment valve 49 and a low pressure adjustment valve 39 may be used to adjust the pressure of the air being delivered to the patient. The high pressure air flow 47 from the high pressure chamber 45 and the low pressure air flow 37 from the low pressure chamber 35 may thereby be regulated. The high and low pressure valves 49 and 39 respectively may be controlled by a controller or microprocessor 82 or set manually on control panel 110 as inspiration pressure control 120 and expiration pressure control 125. Alternatively in another embodiment the motor 20 speed is adjusted to provide the desired pressure in the high pressure chamber 45 and in the low pressure chamber 35 eliminating the need for valves.

The outlet nozzle 48 is a split nozzle extending from the housing 25 over the housing barrier 40 such that both high pressure air 47 the adjacent low pressure air 37 flow in their respective halves of the nozzle to a split coupler 58 having two sides.

A dual pressure hose 50 connects to the coupler 58. The dual pressure hose 50 has a high pressure side 51 and a low pressure side 52 for transporting the high pressure gas 47 and low pressure gas 37 to the mask 70.

Alternatively the dual pressure 50 hose can be a small diameter hose inside of a larger diameter hose for transporting the separate pressures from the housing to the mask, or two separate hoses can be used.

A valve 60 at the entrance to the mask 70 alternately selects the high pressure air 47 or low pressure air 37 to be supplied to the patient 100 depending on if the patient is inhaling or exhaling. When the patient 100 is inhaling the valve 60 selector 62 blocks the low pressure air in the low pressure portion 52 of hose 50 and admits the high pressure from the high pressure portion 51 of hose 50. Similarly when the patient 100 is exhaling the valve 60 selector 62 blocks the high pressure portion 51 of hose 50 and admits low pressure air. An actuator 63 moves the selector 62 based on information about the patient's breathing obtained from sensors 71 in the mask 70 and or sensors 80 placed on the patient 100. The controller or microprocessor 82 determines when the patient 100 is inhaling or exhaling from the data provided and positions the actuator 63 accordingly by sending it signals over lead 83.

The valve 60 may be a split butterfly valve, a gate valve or any other type of valve for selectively admitting only one pressure.

In one embodiment for controlling the pressure to the mask 70 a valve 60 such as a butterfly valve can be partially open to the high pressure chamber 45 and partially open to the low pressure chamber 35 simultaneously, resulting in a mix of between 0 and 100% of each pressure to select an intermediate pressure to the mask. The valve 60 can be quickly activated to any setting to provide any pressure between the high pressure in the high pressure chamber 45 and the low pressure in the low pressure chamber 35.

Alternatively a hose 50 with one lumen can be used and the valve 60 for selecting high or low pressures can be at the outlet nozzle 48. The hose 50 will then contain either a high pressure air flow 47 or a low pressure air flow 37 to the mask 70.

The sensors 71 used for supplying information about the patient's breathing to the controller or microprocessor 82 may be imbedded in the perimeter of the mask 70 or on the mask surface. Such a mask 70 and the types of sensors used are described in the applicant's copending patent application titles Bio-Mask Ser. No. 09/465,054 filed Dec. 16, 1999 which is hereby made a part hereof and incorporated herein by reference.

In one embodiment a sensor 71 on the mask or in the dual pressure gas delivery device 10 can detect when breathing into the mask begins or when mask 70 is donned by a patient to automatically turn on the power to the motor 20.

The sensors 71 can detect leaks or drops in pressure and send signals to microprocessor 82 to increase the pressure sent to the mask 70 to compensate for the leaks.

Sensors 71 can also detect the expiration gases to see if the patient is rebreathing his breath. The microprocessor 82 is programmed to adjust valves in the mask or pressures to the mask to prevent rebreathing.

Other sensors on the patient such as sensor 80 on the patient's chest may be used for supplying information about the patient's breathing to the controller or microprocessor 82.

Some means for the detection of inspiration and expiration are shown in applicant's PCT applications WO 98/50095, entitled Controlling Gas of Drug Delivery to a Patient, international filing date May 7 1997, and in WO 97/16216 entitled Apparatus for Gas Delivery, international filing date Oct. 31, 1996. Other patents teaching breathing measurements are U.S. Pat. Nos. 4,440,177 and 4,463,764. All of the above patents and applications are attached hereto and incorporated herein by reference.

Other means for detecting breathing are by measuring air flow movements to the mask 70 from the air supply such as sensors like 195 placed at the entrance to the mask 70. The sensors 195 may be laser sensors, radar Doppler sensors, ultrasonic sensors, ultrasound techniques, pitot tubes, or other electronic or mechanical means for measuring the air passing the sensor. Other means for measuring air flow rates and breathing are available such as shown in U.S. Pat. No. 5,038,733 entitled Flow Meter System issued Aug. 13, 1991 and U.S. Pat. No. 4,796,639 entitled Pulmonary Diagnostic System, issued Jan. 10. 1989 both of which are attached hereto and made a part hereof by reference.

The dual pressure gas delivery device 10 can be used to select only high pressure gas at all times to provide treatment of Continuous Positive Air Pressure (CPAP) with CPAP protocols. Similarly, with suitable programming of the controller 82, the dual pressure gas delivery device 10 can be used for Variable Positive Air Pressure (VPAP) treatment protocols, Sleep linked Positive Air Pressure (SPAP) treatment protocols, Proportional Positive Air Pressure (PPAP)

treatment protocols, Auto Positive Air Pressure (AuotPAP) or other treatment protocols by using the protocol selection feature 175 on the control panel 110 and having the controller 82 programmed for delivering gas at the proper gas pressures at the proper times.

In some treatment protocols there is a ramp time where the pressure is slowly increased to the desired pressure for treatment over time as the patient falls asleep. The dual pressure gas delivery device 10 has a controller/microprocessor 82 which can be programmed for ramp times and pressures as required by the patient. A ramp time control knob 130 on the control panel can also be used to select the ramp times. Ramp delay times are used in conjunction with ramp times. The ramp delay times allow a time before the ramp up of pressure begins, allowing the patient to fall asleep before the treatment begins. The ramp delay times can be selected on the control panel 110 by ramp delay time control selector 135.

The ramp times, ramp delay times and other parameters can be programmed into the controller/microprocessor 82 by means of information stored on a data card 210 inserted into a data card port 115. Alternatively the controller/microprocessor 82 may be programmed by a computer 200 and the information transferred to the controller/microprocessor 82 through computer input output plug 118. The computer 200 may be remotely located at a hospital or sleep clinic and connected through the internet by wire or wireless phone systems or positioned adjacent the dual pressure gas delivery device 10.

Alternatively a keypad 173 can be used to enter data into the microprocessor/controller 82 for patient data information, or to select times, pressures or other parameters for running the dual pressure gas delivery device. A menu on display 170 driven by controller 82 may prompt the user to enter data for settings by use of the keyboard 173.

Other settings on the control panel 110 are for comfort settings 180 in which the temperature, pressure, humidity and timing of the application of pressurized air to the patient is controlled. The comfort setting may also be stored on the data card 210 or in the controller 82, or computer 200 to provide the best comfort setting for the type of treatment individualized for the patient.

The control panel 110 or other portion of the device can have an on off switch 190 easily accessible by the patient for turning the device 10 on and off.

The control panel can have a display panel 170 such as an LCD for displaying information about the patient, the performance parameters of the dual pressure gas delivery device 10, such as an hour meter for how long the motor 20 has been on, an elapsed time at pressure meter, an elapsed running time meter or other information. Such information can be selected for display by a selection button on the control panel 110, by a touch screen LCD or by other means. The information selected can be transmitted from the controller/microprocessor 82, to the display panel 170 or can be recorded or stored on a smart card 210 or the microprocessor 82 and can be transmitted to a computer 200.

Different sleep disorder treatments use different trigger points to start the application of the high pressure during inspiration. A spontaneous trigger point measures the patient's spontaneous respiratory effort to trigger the application of gas to the patient when he starts to inhale. A timed trigger point uses a predetermined rate to trigger the application of gas to the patient.

Adjustable trigger points can be set in the controller 82 or on the control panel 170 to vary the pressures at which the patient begins to receive air either during inspiration or expiration Poor synchronization between the patient's and the machine's 'breathes' lead to an unwanted increase in the work of breathing by the patient, reduced comfort and, subsequently detrimental/reduced therapy. Therefore it is important to have sensors 71, 80 providing data to a controller 82 for application of the proper pressure at the proper time to treat the patient 100. It is also important in BiPAP applications for the air supply to be at the right pressures in the mask 70 at the right time. In order to accomplish this one motor 20 spinning at one rate can supply two pressures to a mask 70 with a selector 62 alternating between the high and low pressures as the patient inhales and exhales. The motor speed can be increased or decreased to provide higher or lower pressures for inhaling and exhaling.

Communications from the sensors 71, 80 can be by leads 83, 81 respectively or by telemetry to the controller 82.

The controller 82 can be programmed remotely by telemetry, through transmitter receiver 87, or by wire to a port 118 to plug in a data line from a computer 200 to the controller 82. The controller 82 can also be programmed by a data card 210 inserted into data card port 115 to transfer instructions to the controller 82.

The port 118 can also be used to receive data from the controller 82 obtained from the sensors 71, 80 and send it to the computer 200 for use by health care workers.

For example the sensors 71, 80 may collect data about breathing volumes, breathing rates, breathing times, blood oxygen, EEG, EKG, EOG, EMG, patient pulse, patient temperature, snoring, position of the patient, sleep stages, patient movement, mask pressures, mask leakage, and other relevant data such as would be collected for a Polysomnogram (PSG). Such data for treating the patient may be sent by leads or by telemetry to the controller 82 for processing and storage. Patient data may be used to treat the patient in real time or be stored and studied at a later time. The data may be transmitted to a computer 200 at a remote location such as a doctor's office or hospital for remotely monitoring the patient. The computer 200 can store data about the patient which can be presented to a health care provider to diagnose or treat the patient. The data stored about a patient can be used over long term studies and can print out progress reports about the patient. Further is a patient is taking part in a study with a group of other patients the data is readily available to be used in the data for the study.

Connections to the computer 200 can be by telemetry such as by Blue Tooth®, a cell phone data transmittal protocol, or over telephony networks through data port 118.

Telemetry devices used to transmit and store multiple channels of data are available under the trade name Siesta® by Compumedics Inc. Abbotsford, VIC, Australia.

The dual pressure gas delivery device 10 is preferably compatible with Telemed® or other remote medical systems such that the patient can use the dual pressure gas delivery device 10 at home and still have the support of health care providers located remotely. This device will help free sleep disorder patients from having to be at a hospital or other health care facility while being treated or tested.

Other means for data storage are by a data card or smart card 210 which can store data about a patient, or provide data about the patient or for programming the controller 82. The data card or smart card is inserted into card port 115 to access the dual pressure gas delivery device 10.

Input means for data or selections to control the dual pressure gas delivery device 10 through control panel 110 can be by selecting settings from any array of control knobs on the control panel 110, by a menu driven touch screen on display 170 in conjunction with controller 82, or by other input/output devices as are currently known and used in the art.

A sensor or sensors in or on a mattress the patient is on may be connected to the controller 82 to provide data about patient movements and activity rates.

There is a need for a mask off alarm or mask leak alarm to tell the patent or health care worker that the mask is not delivering air to the patient properly. Such detectors are taught in the patents incorporated herein by reference. When the mask off or mask leak alarm 165 is activated the mask should be checked and the alarm deactivated. Sensors 71 in the mask 70 can detect if the mask has come off of the patient and send a signal to the microprocessor 82. The microprocessor can sound an alarm 165 or alert a health care worker that the mask is off. The microprocessor 82 may shut down the motor 20 if mask 70 is off.

The dual pressure gas delivery device 10 can be used for monitoring and treatment of many sleep disorders. The computer 200, microprocessor 82 or data card 210 can store date about the duration, start times and stop times of the treatment, the pressures used, air flow rates and patient data such as heart rates, blood oxygen rates, snoring, patient movement and other polysomnogram data useful in diagnosing and treating patients.

Obviously, many modifications and variations of the present invention are possible in light of the above teachings. It is therefore to be understood that, within the scope of the appended claims, the invention may be practiced otherwise than as specifically described.

What is claimed is:

1. A dual pressure gas delivery device comprising:
   a motor having a shaft extending from the motor, the shaft having at least one impeller for producing a first air pressure and a second air pressure,
   a housing having a first chamber and a second chamber wherein the first air pressure enters the first chamber, and the second air pressure enters the second chamber,
   each chamber having an air exhaust aperture such that air having a first pressure exits the air exhaust aperture of the first chamber and air having a second air pressure exits the air exhaust aperture of the second chamber.

2. A gas delivery device as in claim 1 wherein:
   one impeller on the shaft increases the pressure of the air for both chambers,
   the housing has a slot along the length of the impeller leading to the first chamber for providing a first air pressure in the first chamber,
   the housing has an opening at the end of the impeller for providing a second air pressure in the second chamber.

3. A gas delivery device as in claim 1 wherein:
   a first impeller and a second coaxial impeller produce the first and second air pressures introduced to the first and second chambers at the ends of the impellers.

4. A gas delivery device as in claim 1 wherein:
   two impellers on different portions of the shaft produce the first and second air pressures introduced to the first and second chambers at the ends of the impellers.

5. A gas delivery device as in claim 1 comprising:
   a mask for applying gas to a patient,
   a means for transporting the air from the first chamber and the second chamber to the mask,
   a means for selecting either the first air pressure or the second air pressure to be admitted to the mask.

6. A gas delivery device as in claim 5 wherein:
   the means for selecting either the first air pressure or the second air pressure to be admitted to the mask comprises an actuator, attached to the means for transporting the air to the mask, for moving a selector to block the air from one of the chambers while allowing the air from the other chamber to pass.

7. A gas delivery device as in claim 6 wherein:
   a means for instructing the actuator to select an air pressure such that a high air pressure is applied to the mask during inspiration and a low pressure is applied to the mask during expiration.

8. A gas delivery device as in claim 7 wherein:
   the means for instructing the actuator to select an air pressure comprises a controller sending signals to the actuator, and at least one sensor for obtaining information from the patient about his breathing such that the controller can process the information to determine if the patent is inhaling or exhaling and send the signals to the actuator accordingly.

9. A gas delivery device as in claim 1 having:
   a mask for applying gas to a patient,
   a means for transporting the air from the first chamber and from the second chamber to the mask,
   a means for selecting a portion of the first air pressure and a portion the second air pressure so that they can be mixed to create a third air pressure to be admitted to the mask.

10. A gas delivery device as in claim 9 wherein:
    the means for selecting a portion of the first air pressure and a portion of the second air pressure so that they can be mixed to create a third air pressure to be admitted to the mask comprises a butterfly valve for simultaneously partially blocking the first air pressure and partially blocking the second air pressure to derive a third air pressure.

11. A gas delivery device as in claim 1 having:
    a means for varying the ratio of pressures in the high pressure chamber and low pressure chamber.

12. A gas delivery device as in claim 1 having:
    a means for varying the speed of the at least one impeller to change the pressure in the high pressure chamber and in the low pressure chamber.

13. A gas delivery device as in claim 1 wherein:
    a humidifier adds humidity to the air in at least one chamber.

14. A gas delivery device as in claim 1 having;
    an air filter that filters the air of at least one chamber.

15. A gas delivery device as in claim 1 wherein:
    a handle on the device for ease of transport.

16. A gas delivery device as in claim 1 wherein:
    a pressure adjustment valve on the first air chamber exhaust aperture allows for adjusting the air pressure exiting the chamber.

17. A gas delivery device as in claim 16 wherein:
    a pressure adjustment valve on the second air chamber exhaust aperture allows for adjusting the air pressure exiting the chamber.

18. A gas delivery device as in claim 17 wherein:
    a first actuator controls the pressure adjustment valve for the pressure on the first chamber,
    a second actuator controls the pressure adjustment valve for the pressure on the second chamber, and
    both the first and second actuators are controlled by a controller.

19. A gas delivery device as in claim 8 wherein:

a pressure adjustment valve on the first air chamber allows for adjusting the air pressure exiting the chamber.

20. A gas delivery device as in claim 19 wherein:

a pressure adjustment valve on the second air chamber allows for adjusting the air pressure exiting the chamber.

21. A gas delivery device as in claim 20 wherein:

a first actuator controls the pressure adjustment valve for the pressure on the first chamber, a second actuator controls the pressure adjustment valve for the pressure on the second chamber, and both the first and second actuators are controlled by the controller.

22. A gas delivery device as in claim 5 wherein:

the device has a means for selecting the pressure of the high pressure air delivered to the mask.

23. A gas delivery device as in claim 5 wherein:

the device has a means for selecting the pressure of the low pressure air delivered to the mask.

24. A gas delivery device as in claim 5 wherein:

the device has a means for selecting ramp times and ramp time delays for the air delivered to the mask.

25. A gas delivery device as in claim 5 wherein:

the device has a means for selecting the protocol used for delivering air to the mask such that different treatments can be applied to the patient with the same device.

26. A gas delivery device as in claim 5 having:

a data card port connected to a controller such that a data card inserted into the data card port can send data to and receive data from the controller.

27. A gas delivery device as in claim 5 wherein:

an input output data port connected to a controller such that data can be sent to and received from the controller at a remote site from the device.

28. A gas delivery device as in claim 5 wherein:

a transmitter and receiver connected to a controller such that data can be sent to and received from the controller.

29. A gas delivery device as in claim 5 wherein:

a keypad connected to a controller enters data to the controller such that settings for the controller are selected.

30. A gas delivery device as in claim 5 wherein:

a control panel on the device connected to a controller such that data can be sent to and received from the controller from the control panel.

31. A gas delivery device as in claim 30 wherein:

the control panel has an LCD display.

32. A gas delivery device as in claim 1 wherein:

the motor is a brushless DC motor such that no ozone or NOx is produced.

33. A gas delivery device as in claim 1 having:

a means for tracking elapsed time.

34. A gas delivery device as in claim 33 having:

a means for displaying elapsed time.

* * * * *